United States Patent [19]

Angelsen et al.

[11] Patent Number: 5,465,723
[45] Date of Patent: Nov. 14, 1995

[54] METHOD AND APPARATUS FOR ULTRASOUND IMAGING

[75] Inventors: Bjorn Angelsen; Michael Nickel, both of Trondheim, Norway

[73] Assignee: Vingmed Sound A/S, Horten, Norway

[21] Appl. No.: 252,951

[22] Filed: Jun. 2, 1994

[51] Int. Cl.⁶ ........................................................ A61B 8/00
[52] U.S. Cl. ........................................................ 128/661.02
[58] Field of Search ........................ 128/660.06, 660.07, 128/660.08, 660.09, 661.02, 663.01

[56] References Cited

U.S. PATENT DOCUMENTS

5,320,106  6/1994  Tanaka ................................ 128/663.01

Primary Examiner—George Manuel
Attorney, Agent, or Firm—Cohen, Pontani, Lieberman, Pavane

[57] ABSTRACT

Ultrasound imaging of an object is effected by directing a first and a second ultrasound pulse emitted by a transducer along a beam propagation direction against an object to be imaged. The second pulse has a transducer-to-object propagation time greater than the first pulse, the propagation time difference being achieved by selectively varying the effective or acoustic distance between the transducer and the object. A second scanline signal returned from the object as an echo of the second pulse is time-shifted as a function of the propagation time difference and is subtracted from the first scanline signal returned from the object as an echo of the first pulse, thereby significantly reducing from the resulting signal reverberation echoes between the transducer and the object. Transducer arrangements for providing the relative propagation time difference of the first and second pulses operatively vary the acoustic distance between the transducer and the object.

24 Claims, 5 Drawing Sheets

METHOD AND APPARATUS FOR ULTRASOUND IMAGING

FIELD OF THE INVENTION

The present invention relates to the use of ultrasound for non-invasive imaging of biological tissue and non-destructive testing of materials and, more particularly, to methods and apparatus for suppressing reverberation echoes that occur in such uses of ultrasound.

BACKGROUND OF THE INVENTION

Ultrasonic imaging advantageously permits the real-time visualization of biological tissue structures within a human or animal body and, in addition, allows the non-destructive testing of materials. For convenience, a body or material to be imaged or tested is referred to herein as the object. In ultrasonic imaging an electronically-reconstructed or viewable image is typically generated by scanning or sweeping a pulsed ultrasound beam across the object to perform pulse echo reflection imaging of structures present within the object.

One problem with ultrasonic imaging, however, is that the reception of ultrasound echoes is subject to inherent acoustic noise. Reverberation echoes—i.e. second order reflections—constitute a strong and significant portion of this acoustic noise. The term reverberation refers to an ultrasound pulse that is reflected back and forth between internal tissue/material structures (i.e. internal reverberations) or between such tissue/material structures and the transducer surface (i.e. transducer-tissue/material reverberations). In image reconstruction or generation it is assumed that each echo comes directly from a scatterer that is hit by the propagating pulse emitted by the transducer. This assumption, however, results in the unfortunate misinterpretation of multiple-reflection echoes and thus constitutes acoustic noise.

A special transducer design incorporating a $\lambda/2$ matching layer is described in the *Proceedings of the 19$^{th}$ International Symposium on Acoustical Imaging,* at pp. 219–33 (1991). That transducer design is intended to minimize the reflection factor at the transducer surface so as to reduce reflections of received pulses at the transducer surface and hence reduce reverberation echoes.

A method of reducing reverberation echoes by dual frequency image subtraction is described in 12 *IEEE Transactions On Medical Imaging,* pp. 792–802 (1993). A particularly serious drawback to the dual frequency image subtraction method of reducing reverberation noise is that, in addition to internal reverberations, the received first order back-scattered echo signals are also attenuated.

SUMMARY OF THE INVENTION

It is accordingly the principal object of the present invention to improve the quality of ultrasound images of biological tissue, and of ultrasound images of materials examined in non-destructive testing, by suppressing reverberation echoes between strong reflectors in the object (i.e. tissue/material) and the ultrasound transducer. This intended goal is achieved by acquiring the ultrasound RF-signal echoes or scanlines from two transducer-delivered ultrasound pulses having the same beam direction but differing propagation times or lags or delays between the ultrasound pulse-emitting transducer and the object under test—i.e. each of the two pulses takes a different amount of time to reach and enter the object under test, the difference of the two propagation times being either a preset or predetermined or calculatable quantity. The difference between the respective propagation times of the two pulses is referred to herein as the propagation lag difference or propagation difference between the two transducer-delivered pulses. The desired or intended propagation lag difference between the two scanlines may, by way of example and in accordance with certain currently-preferred aspects of the invention, be obtained by varying the distance between the transducer and the object for one pulse relative to the other, or by inserting between the transducer and object one or more phase plates exhibiting different wave velocities. The received ultrasound RF-signal echo or scanline from the first pulse is stored electronically and is then combined with the received ultrasound RF-signal echo or scanline from the second pulse to reduce the presence in the scanlines of reverberations occurring between strong reflectors in the object and the transducer.

In one particular implementation or embodiment of the invention, the received RF-signal scanline or echo from the second pulse is time-shifted by twice the delay corresponding to the propagation lag difference between the two pulses. In this manner, the time lags of the reverberation signals or second-order echoes of the two scanlines is matched. Subtracting the back-shifted second scanline from the first scanline yields the reverberation-reduced signal which is input to further state of the art or otherwise suitable processing to derive an ultrasound image.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote similar elements throughout the several views.

DETAILED DESCRIPTION OF THE PREFERRED EMBODIMENTS

Figure 1:
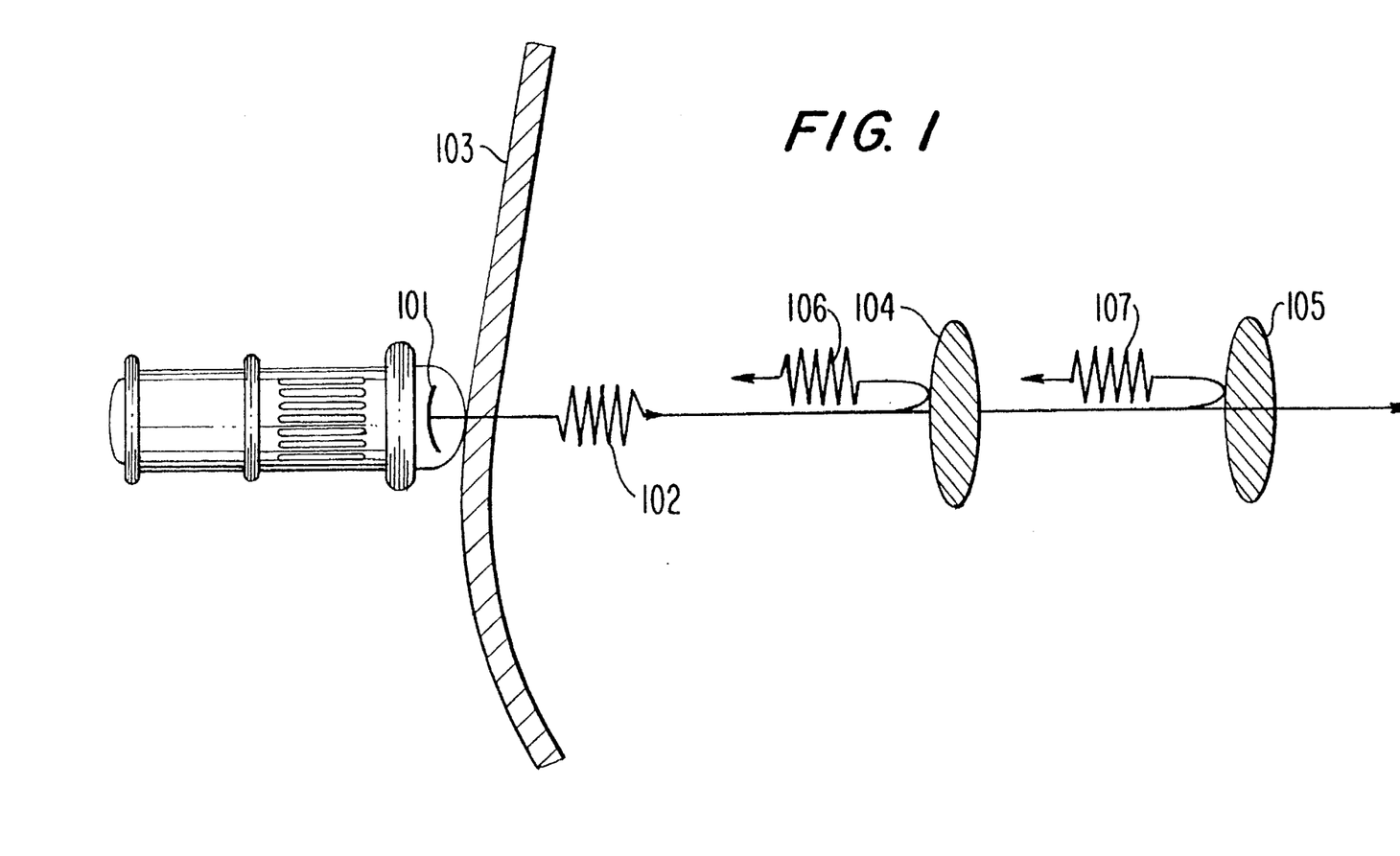
FIGS. 1 and 2 diagrammatically depict illustrative instances of ultrasonic pulse propagation and reflection in an object under examination.
Figure 2:
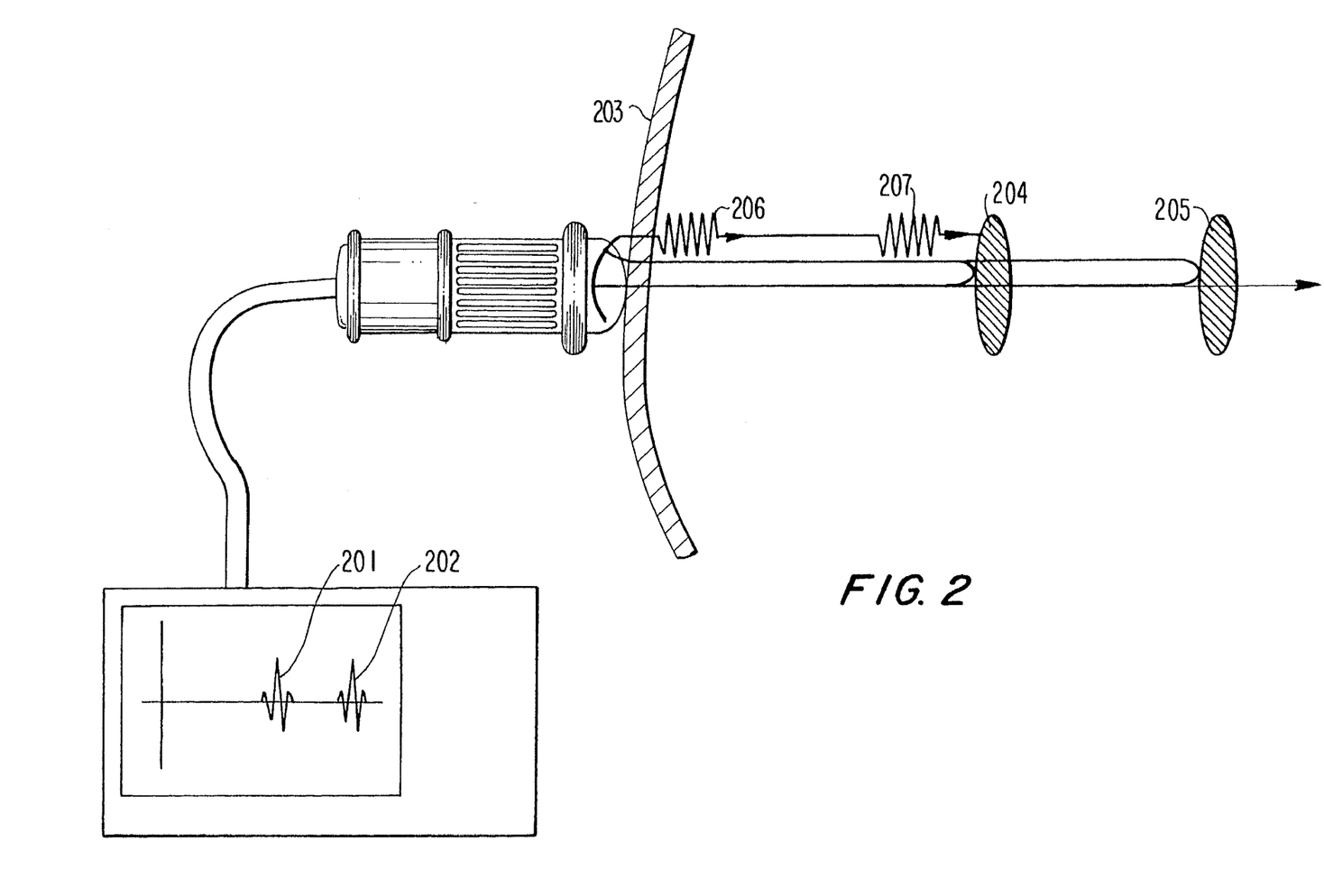

Depicted in FIG. 1 is an ultrasound transducer 101 transmitting an ultrasonic pulse 102 that is seen to have entered an object 103. The pulse is reflected from two targets 104, 105 located within the object 103, thereby generating the respective first order echo pulses 106, 107. In FIG. 2 these first order echoes are shown as having returned to the transducer surface, where they are partially transmitted through the surface to generate the received ultrasound RF-echo signals 201, 202 and partially reflected from the surface to form the reverberation pulses 206, 207 which propagate back into the object 203. As a result of that further reflection, the targets 204, 205 are unintendedly imaged once more by the reverberation pulses 206, 207, thus producing second order reverberation echoes that are superimposed on the signal of the first order echoes and which thereby disturb and partially mask the signal.

Assuming a constant velocity of sound c, there is a direct relationship between the elapsed time t for a transducer-transmitted pulse to travel or propagate to a scatterer located at a range r and the return of the echo or reflection to the transducer. That elapsed time t may be calculated as follows:

$$t = \frac{2r}{c} \qquad \text{Eq. 1}$$

Thus, the elapsed time variable t may be replaced by the range variable r to determine the range distance to the image. All echo signals arriving at the same time are accordingly interpreted as originating from, and are displayed as being located at, the same range or location—including the reverberation echoes which have made the return trip between the transducer and the scatterers not once but two or more times. These reverberations thus appear as acoustic noise in the resulting image.

The first order electrical echo signal v(r) of a scatterer distribution σ(r) along the beam axis is defined in a one-dimensional model by the real part of the analytical signal as $$v(r) = \alpha_1 \cdot e^{j2k_o r} \cdot P_e(r) * \sigma(r) \qquad \text{Eq. 2}$$

Here, * denotes convolution. The term $e^{j2k_o r} \cdot P_e(r)$ represents the transmitted RF-pulse with complex envelope $P_e(r)$ and complex phase factor $e^{j2k_o r}$ rotating at a spatial frequency $2k_o$, which corresponds to the temporal frequency $f_o = (k_o c)/2\pi$, and the factor $\alpha_1$ represents the net gain. The attenuation of the ultrasound in the object is assumed to be included in the target distribution σ(r), and the reverberation pulses arise when the first order echoes arrive at the transducer. As compared to the transmitted pulse 102, the reverberation pulses are delayed by the travel time to their targets and back, and are attenuated in accordance with the medium through which they are traveling. Thus, the reverberation impulse response in this model is given by $\beta \cdot \alpha_1 \cdot e^{j2k_o r} \cdot P_e(r) * \sigma(r)$, where β represents the reflection factor at the transducer surface. The second order or reverberation pulse echo may thus be represented by $$v_{rev}(r) = \alpha_2 \cdot e^{j2k_o r} \cdot P_e(r) * \sigma(r) * \sigma(r) \qquad \text{Eq. 3}$$

with $\alpha_1 = \alpha_2 \cdot \beta$. And the received signal, with the first order and reverberation echoes superimposed, may be correspondingly represented by the relationship $$v_{tot,1}(r) = \alpha_1 \cdot e^{j2k_o r} \cdot P_e(r) * \sigma(r) + \alpha_2 \cdot e^{j2k_o r} \cdot P_e(r) * \sigma(r) * \sigma(r) \qquad \text{Eq. 4}$$

Next to be considered are the effects arising when the propagation time between the transducer and the object 203 is changed or varied—i.e. so that the time for a transducer-originating pulse to reach the object 203 is changed—by displacing the transducer a distance Δr along the axis. It should be noted that the same change in propagation time can alternatively be achieved by placing a phase plate with a different ultrasound velocity in front of the transducer; this alternative implementation is further discussed hereinbelow.

The axial translation of the transducer to introduce the intended propagation lag or delay must be performed in such a way that the object 203 under examination is not deformed—i.e. so that the target structure, although remaining the same, is merely displaced relative to the transducer along the axis by Δr. This means that the term σ(r) in Equation 4 must be replaced by σ(r+Δr), yielding $$v_{tot,2}(r) = \alpha_1 \cdot e^{j2k_o r} \cdot P_e(r) * \sigma(r+\Delta r) + \alpha_2 \cdot e^{j2k_o r} \cdot P_e(r) * \sigma(r+\Delta r) \sigma(r+\Delta r) \qquad \text{Eq. 5}$$

which is equivalent to $$v_{tot,2}(r) = \alpha_1 \cdot e^{j2k_o r} \cdot P_e(r) * \sigma(r) * \delta(r+\Delta r) + \alpha_2 \cdot e^{j2k_o r} \cdot P_e(r) * \sigma(r) * \sigma(r) * \delta(r+2\Delta r) \qquad \text{Eq. 6}$$

It is thus seen that the change in image position of the first order echo is Δr, and for the second order echo or reverberation in the image is 2Δr. The present invention makes use of this relationship to reduce or suppress reverberation echoes between strong reflectors in the object under test and the ultrasound transducer.

Shifting the relatively delayed signal $v_{tot,2}(r)$ back by two times Δr (i.e. by 2Δr) will match the reverberation signal in $v_{tot,2}(r)$ to the reverberation component in the non-delayed signal $v_{tot,1}(r)$, as seen in the following Equation 7:

$$\begin{aligned} v_{tot,2;shifted}(r) &= v_{tot,2}(r) * \delta(r - 2\Delta r) \\ &= \alpha_1 \cdot e^{j2k_o r} \cdot p_e(r) * \sigma(r - \Delta r) + \\ &\quad \alpha_2 \cdot e^{j2k_o r} \cdot p_e(r) * \sigma(r) * \sigma(r) \end{aligned} \qquad \text{Eq. 7}$$

Subtracting the two scanline signals, one from the other, then yields the following new, reverberation-suppressed RF-signal $v_{canceled}(r)$:

$$\begin{aligned} v_{canceled}(r) &= v_{tot}(r) - v_{tot,2;shifted}(r) \\ &= \alpha_1 \cdot e^{j2k_o r} \cdot [p_e(r) - e^{-j2k_o \Delta r} p_e(r - \Delta r)] * \sigma(r) \end{aligned} \qquad \text{Eq. 8}$$

These Equations describe the theoretical underpinnings of the invention. Several illustrative practical embodiments of apparatus constructed in accordance with the teachings of the invention are now presented.

Figure 3:
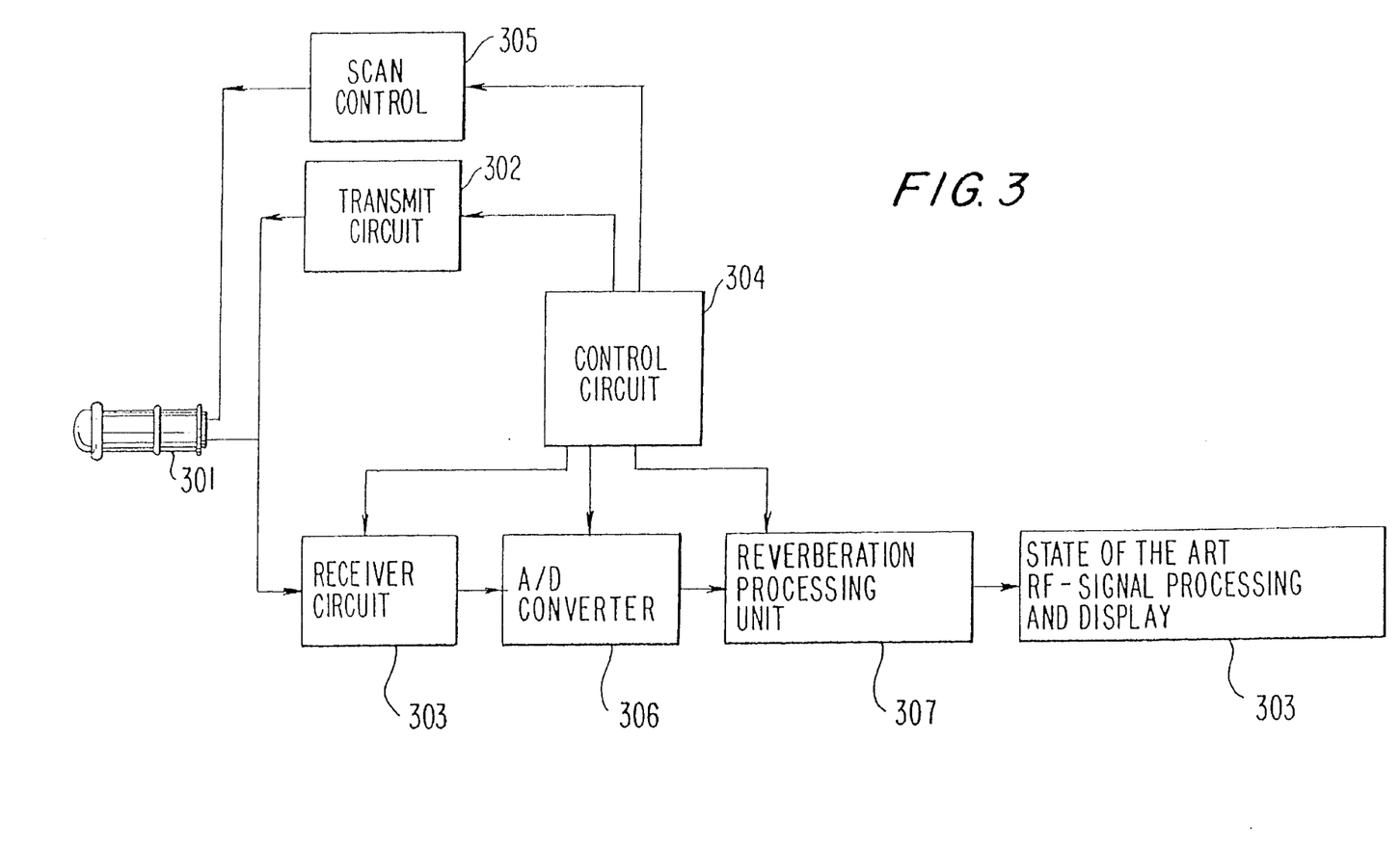
FIG. 3 is a block diagram depicting an embodiment of an ultrasonic imaging system constructed in accordance with the teachings of the present invention.

FIG. 3 is a block diagram of an apparatus operable for acquiring and displaying reverberation-reduced ultrasound data in accordance with the present invention. The transmit circuit 302 initially activates the transducer mounted in probe 301 to transmit a pulsed ultrasound beam under the direction of a scan control device 305. The returning ultrasound echoes (i.e. the scanline) are transformed or converted by the transducer into analog electrical signals and transferred to the receiver circuit 303 at which those signals are amplified. The amplified analog ultrasound RF-signal is then converted to digital form by the A/D (analog-to-digital) converter 306 and fed to the reverberation processing unit 307. The output of the unit 307—which in accordance with the present invention is obtained through the processing, as herein disclosed, of the scanlines from two same-direction, transducer-generated pulses related by the aforedescribed propagation lag difference—may then be transferred to a conventional or otherwise suitable processing and display device 308 for generating a reverberation-reduced ultrasound image of the object under test. A control circuit 304 is operable for organizing and directing the aforedescribed data acquisition and processing operations and procedure among the various devices and elements of the apparatus. As should be apparent, the methods and apparatus of the present invention may be used with both mechanical and/or electronic steering of the ultrasound beam as a general matter of design choice.

Figure 4:
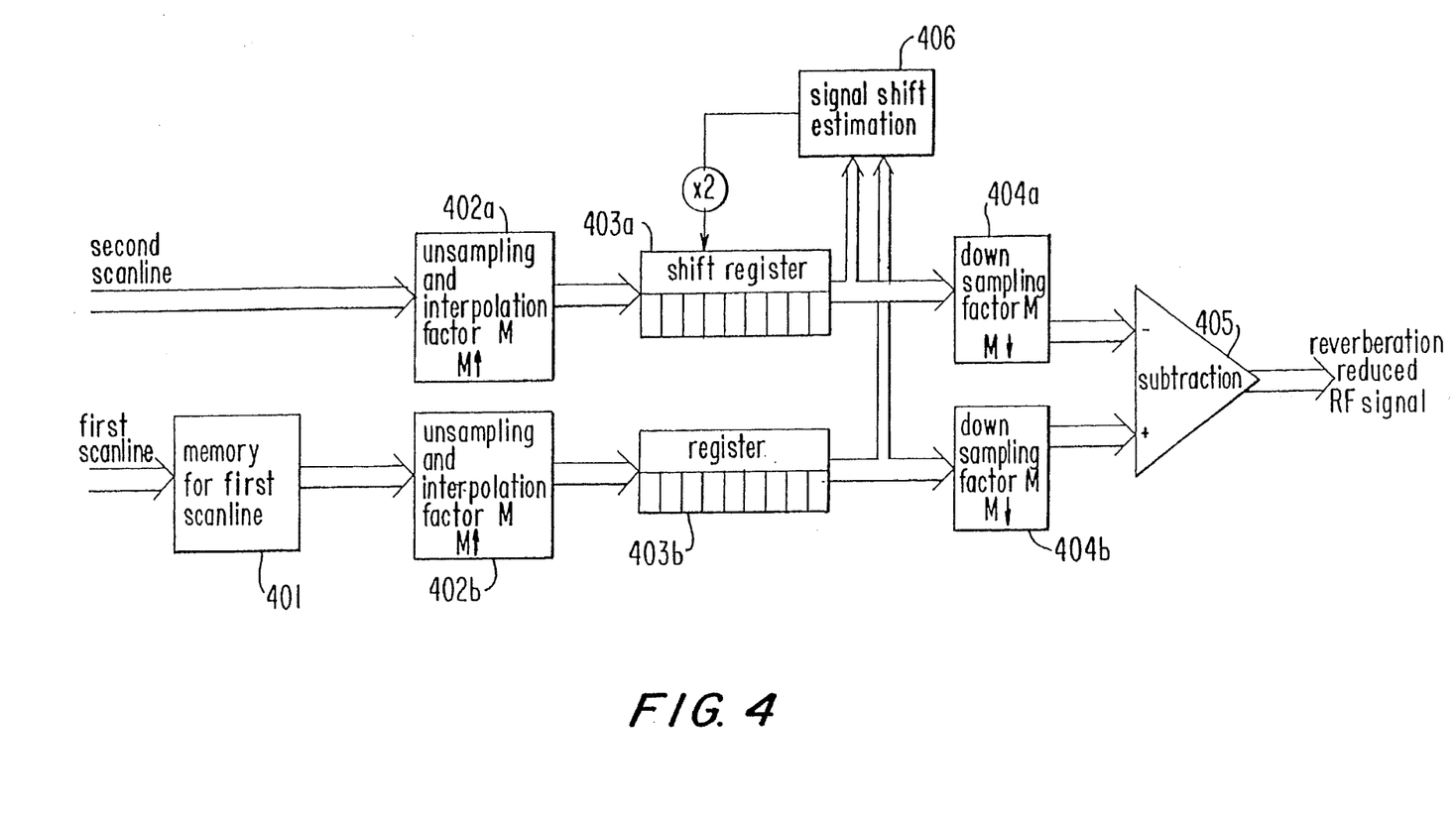
FIG. 4 is a block diagram depicting an embodiment of a reverberation processing unit in accordance with the invention.

A detailed block diagram of the reverberation processing unit 307 of FIG. 3 is illustrated in FIG. 4. To begin, the first scanline (from the first ultrasound pulse) is loaded into memory 401. During the subsequent acquisition of the second scanline (from the propagation-delayed second ultrasound pulse) for the same beam direction, the first scanline is read out from the memory 401 in parallel with the second scanline. In a preferred form of the unit 307, the sampling rate of both scanlines is upconverted in sampling rate by a factor M at the blocks 402a for the first scanline and 402b for the second. This upconversion in sampling rate allows highly accurate time shifting of the second scanline to an accuracy below the original sampling rate. The time shift of the second scanline is performed at the shift register block 403a after the magnitude of the propagation lag or delay between the first order echoes is automatically determined at the signal shift estimation unit 406. (It should also be pointed out that the propagation lag difference may alternatively be preset or otherwise selectively predetermined, thereby eliminating the need for its automatic calculation or determination at the signal shift estimation unit 406, or may be dynamically adjusted by the user—as by observing the resulting ultrasound image on an output monitor or the like while the propagation lag difference is varied—to yield the best ultrasound image of the object under test.) The determination of the propagation lag difference at the unit 406 may, for example, be effected by conventional cross-correlation of the two scanline signals. An intermediate storage register 403b may, for convenience, be employed to synchronize the samples of the first and second scanlines. After the time shift accuracy-enhancing upconversion of the sampling rate, the signals are oversampled relative to their bandwidth. To reduce speed requirements of the downstream processing circuits, the scanlines sampling rate may then be down-scaled, as by the factor M, in the down-shifting units 404a, 404b before the second scanline is thereafter subtracted from the first scanline in the subtraction unit 405. This last operation yields the reverberation-reduced RF-signal of the invention, which may then be further processed in accordance with any methods or procedures conventionally employed or otherwise appropriate in ultrasound imaging. Reductions in reverberation noise on the order of, and well in excess of, approximately 3 db are readily attainable in accordance with the present invention.

Figure 5A:
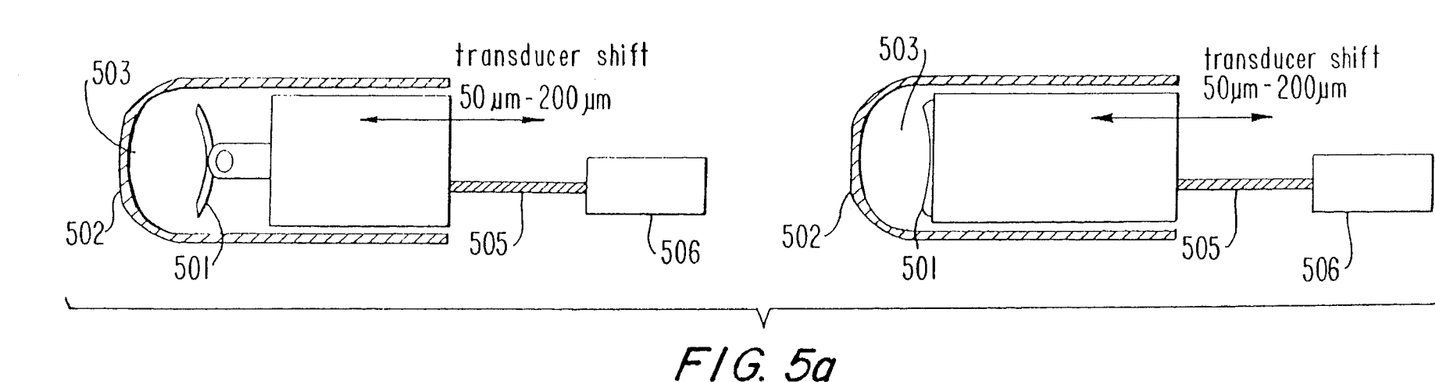
FIGS. 5a and 5b are cross-sectional side views of illustrative embodiments of ultrasound transducer probes constructed in accordance with the invention to provide suitable variations in pulse propagation time between the transducer and the object.
Figure 5B:
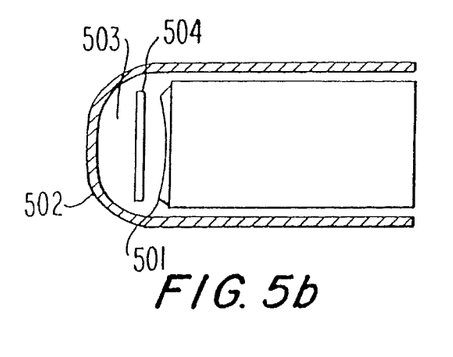

Two methods, and suitable apparatus, for selectively varying the propagation lag difference of the two ultrasonic pulses—i.e. the effective or acoustic distance between the transducer and the biological tissue or other material(s) being imaged—are shown in FIG. 5. In FIG. 5a the transducers 501—which may employ mechanical or electronic beam steering as a general matter of design choice—are contained within a housing dome 502 that is filled with an acoustically transparent fluid 503. The propagation lag difference of the two scanlines is achieved or adjusted by changing the distance, along the beam direction axis, between the transducer and the interior surface of the dome for one transducer-emitted pulse relative to the other. Thus, in this first transducer implementation the actual physical distance between the transducer and the object being imaged is varied to thereby change the propagation lag difference of the two scanlines. The physical movement or displacement of the transducer 501 within and relative to the dome 502 may be effected by any suitable apparatus or arrangement as, for example, a mechanical linkage connected to the transducer and to appropriate gearing arrangement(s) and/or motor operator(s) and/or the like under either direct user control or operated by an automated controller. The arrangement of FIGS. 5a and 5b depicts, by way of example, a linkage arm 505 and a displacement operator 506 for moving or shifting the arm 505 so as to adjust the position of the transducer 501 along the beam propagation direction. In any event, the exact construction and selection of such transducer-displacing components and arrangements and the like are for the most part a general matter of design choice for persons of ordinary skill in the art. Indeed, the use of apparatus for similarly physically displacing the object along the beam direction—in lieu of or in addition to the transducer—is also within the intended scope and contemplation of the invention.

In the alternate embodiment of FIG. 5b, the propagation lag difference is achieved by inserting one or more phase plates 504 with different wave velocities between the transducer and dome for at least one of the ultrasound pulses. This results in a change in the apparent or effective or acoustic distance between the transducer and the object, by virtue of which the propagation time of the ultrasound pulses from the transducer to the object is changed. For wave velocities $c_1$ in the fluid and $c_2$ in the phase plate, the following difference in propagation time with and without the phase plate in place is obtained:

$$\Delta t = 2 \left| \frac{T}{c_1} - \frac{T}{c_2} \right| \qquad \text{Eq. 9}$$

where T signifies the thickness of the phase plate. This corresponds to an effective or acoustic transducer displacement along the ultrasound propagation axis of $$\Delta r = c_1 \cdot \Delta t = 2T \left| 1 - \frac{c_1}{c_2} \right| \qquad \text{Eq. 10}$$

Movement of the phase plate 504 into and out of position between the transducer and dome (or otherwise between the transducer and the object to be imaged) may be effected by any suitable arrangement or apparatus, as for example through pivotal mounting of the phase plate by which the pivoted position of the plate is selectively variable by appropriate user-controlled or automated means.

As should be further apparent from the foregoing description, when translating or moving the transducer along the probe axis using an ultrasound beam direction that lies at a given non-zero angle to (and distinct from) the probe axis, the resulting propagation lag difference will further vary with the beam direction angle. Compensation for the additional propagation lag difference resulting from a non-axial direction of beam propagation may be provided by, for example, either adjusting the transducer displacement in accordance with the angle, or varying the relative backshift or time delay of the second scanline in processing the same in accordance with that angle.

It should also be pointed out that, for convenience, the method of the invention has been described herein as anticipating that the two propagation lag difference-related pulses for a single beam direction will be successively generated by the transducer, following which the beam direction will be varied for the next two propagation lag difference-related pulses, and then varied again for the next two propagation lag difference-related pulses, and so on to complete a suitable ultrasound scan or sweep for use in imaging of the object. Nevertheless, it is equally within the intended scope and contemplation of the invention that the inventive method be practiced by generating and storing the scanline signal for each of a plurality of so-called first transducer-emitted pulses at a multiplicity of different beam directions defining an ultrasound sweep, and then generating and receiving the scanline signals for each of a like plurality of so-called second transducer-emitted pulses at the multiplicity of beam directions of the first sweep, the first and second pulses being related by the aforedescribed propagation lag difference of the invention.

Thus, while there have been shown and described and pointed out fundamental novel features of the invention as applied to several preferred embodiments thereof, it will be understood that various omissions and substitutions and changes in the form and details of the disclosed methods and apparatus may be made by those skilled in the art without departing from the spirit of the invention. For example, whether the disclosed propagation delay or lag is applied to the first-in-time pulse or to the second-in-time pulse is irrelevant to the spirit and practice of the invention. It is the intention, therefore, to be limited only as indicated by the scope of the claims appended hereto.

What is claimed is:

1. A method of reducing transducer-object reverberation noise from scanline signals returning from an object as echoes of ultrasound pulses emitted by a transducer and directed against the object for ultrasound imaging of the object, comprising the steps of:
   (A) receiving a first scanline signal from a first ultrasound pulse directed against the object along a beam direction;
   (B) receiving a second scanline signal from a second ultrasound pulse directed against the object along said beam direction; and
   (C) selectively combining said first and second scanline signals so as to substantially reduce from said signals reverberation echoes between the transducer and the object and thereby define a reverberation-suppressed signal for use in imaging of the object.

2. A method of reducing reverberation noise in accordance with claim 1, wherein the second ultrasound pulse has a difference in propagation lag between the transducer and the object relative to the first ultrasound pulse.

3. A method of reducing reverberation noise in accordance with claim 2, wherein said step (C) comprises:
   (i) time-shifting said second scanline signal relative to said first scanline signal; and
   (ii) subtracting said time-shifted second scanline signal from said first scanline signal.

4. A method of reducing reverberation noise in accordance with claim 3, wherein said step (C)(i) further comprises cross-correlating said first and second scanline signals to determine said time-shift.

5. A method of reducing reverberation noise in accordance with claim 3 wherein said first and second scanline signals comprise analog signals, further comprising the steps of (D) converting said received first and second analog scanline signals to first and second digital signals at a first sampling rate, and (E) upconverting the first sampling rate of said first and second digital signals to a second sampling rate greater than said first sampling rate, and wherein said step (C)(i) further comprises determining said time-shift using said upconverted first and second digital signals.

6. A method of reducing reverberation noise in accordance with claim 5, further comprising the step of (F) downconverting the upconverted second sampling rate of said first and second digital signals, and wherein said step (C)(i) further comprises time-shifting said upconverted second digital signal by said determined time shift, and said step (C)(ii) further comprises subtracting said downconverted time-shifted second digital signal from said first digital signal.

7. A method of reducing reverberation noise in accordance with claim 3 wherein said first and second scanline signals comprise analog signals, further comprising the steps of (D) converting said received first and second analog scanline signals to first and second digital signals at a first sampling rate, and (E) upconverting the first sampling rate of said first and second digital signals to a second sampling rate greater than said first sampling rate, and wherein said step (C)(i) further comprises cross-correlating said upconverted first and second digital signals to determine said time-shift.

8. A method of reducing reverberation noise in accordance with claim 7, further comprising the step of (F) downconverting the upconverted second sampling rate of said first and second digital signals, and wherein said step (C)(i) further comprises time-shifting said upconverted second digital signal by said determined time shift, and said step (C)(ii) further comprises subtracting said downconverted time-shifted second digital signal from said first digital signal.

9. A method of reducing reverberation noise in accordance with claim 1, wherein the first ultrasound pulse is emitted by a transducer located at an acoustic distance $d_1$ from the object and the second ultrasound pulse is emitted at an acoustic distance $d_2$ from the object, wherein $d_2-d_1>0$.

10. A method of reducing reverberation noise in accordance with claim 1, wherein the first ultrasound pulse is emitted by a transducer located at a distance $d_1$ from the object and the second ultrasound pulse is emitted at a distance $d_2$ from the object, wherein $d_2-d_1>0$.

11. A method of reducing transducer-object reverberation noise in ultrasound imaging of an object, comprising the steps of:
   (A) emitting from an ultrasound transducer located at an acoustic distance $d_1$ from an object a first ultrasound pulse directed against the object along a beam propagation direction;
   (B) emitting from an ultrasound transducer located at an acoustic distance $d_2$ from the object a second ultrasound pulse directed against the object along said beam propagation direction, wherein $d_2-d_1>0$;
   (C) receiving a first scanline signal returning from the object as an echo of said first ultrasound pulse;
   (D) receiving a second scanline signal returning from the object as an echo of said second ultrasound pulse;
   (E) selectively combining said first and second scanline signals so as to substantially reduce from said signals reverberation echoes between the transducer and the object and thereby define a reverberation-suppressed signal for use in imaging of the object.

12. A method of reducing reverberation noise in accordance with claim 11, wherein said step (E) comprises:
   (i) time-shifting said second scanline signal relative to said first scanline signal; and
   (ii) subtracting said time-shifted second scanline signal from said first scanline signal.

13. A method of reducing reverberation noise in accordance with claim 12, wherein said step (E)(i) further comprises cross-correlating said first and second scanline signals to determine said time-shift.

14. A method of reducing reverberation noise in accordance with claim 11, wherein said step (B) further comprises physically displacing the transducer relative to the object along the beam propagation direction from the location of the transducer at which said first ultrasound pulse is emitted.

15. A method of reducing reverberation noise in accordance with claim 11, wherein each of the first and second ultrasound pulses has a propagation time between the scan-emitting transducer and the object, and wherein said step (B) further comprises changing the propagation time of the second ultrasound pulse emitted by the transducer relative to the propagation time of the first ultrasound pulse.

16. A method of reducing reverberation noise in accordance with claim 15, wherein said step of changing the second ultrasound pulse propagation time comprises inserting between the transducer and the object a selected phase plate having a predetermined wave propagation velocity.

17. Apparatus for ultrasound imaging of an object, comprising:

a transducer operable for emitting ultrasound pulses directed against an object to be imaged along a beam propagation direction;

means for varying a propagation time, between the transducer and object, of an emitted ultrasound pulse;

means for receiving a first scanline signal returning from the object as an echo of a first ultrasound pulse emitted by the transducer and a second scanline signal returning from the object as an echo of a second ultrasound pulse emitted by the transducer;

means for controlling operation of said transducer so as to vary the propagation time between the first and second ultrasound pulses such that the propagation time of the second pulse is greater than the propagation time of the first pulse; and means for processing said received first and second scanline signals to substantially reduce from the signals reverberation echoes between the transducer and the object and define a reverberation-reduced signal for use in ultrasound imaging of the object.

18. Apparatus in accordance with claim 17, wherein said processing means comprises means for time-shifting the second scanline signal relative to the first scanline signal, and means for subtracting the time-shifted second scanline signal from the first scanline signal.

19. Apparatus in accordance with claim 18, wherein said time-shifting means further comprises means for cross-correlating the first and second scanline signals to determine the time-shift.

20. Apparatus in accordance with claim 17, wherein said propagation time varying means comprises means for displacing the transducer relative to the object along the beam propagation direction.

21. Apparatus in accordance with claim 17, further comprising a fluid-filled dome within which said transducer is disposed, and wherein said propagation time varying means comprises means for displacing the transducer within and relative to the dome and the beam propagation direction.

22. Apparatus in accordance with claim 17, wherein said propagation time varying means comprises means for disposing a selected phase plate having a predetermined wave propagation velocity between said transducer and the object.

23. Apparatus for use in ultrasound imaging of an object, comprising:

a transducer operable for emitting an ultrasound pulse directed against an object to be imaged along a beam propagation direction; and a housing within which said transducer is disposed, said housing including a fluid-filled dome through which ultrasound pulses are operatively emitted by and directly, non-reflectively from said transducer along the beam propagation direction and within which said transducer is disposed;

said transducer being disposed in said housing for selective displacement of the transducer within the housing and relative to said dome along the beam propagation direction so as to selectively vary a transducer-to-object propagation time of an ultrasound pulse emitted by the transducer.

24. Apparatus in accordance with claim 23, further comprising means connected to said transducer and operable for selectively displacing said transducer along the beam propagation direction so as to vary the transducer-to-object propagation time of an ultrasound pulse emitted by the transducer.

* * * * *